United States Patent [19]
Flashinski et al.

[11] Patent Number: 6,031,967
[45] Date of Patent: Feb. 29, 2000

[54] DEVICE FOR DISPENSING VOLATILE MATERIALS

[75] Inventors: Stanley J. Flashinski, Racine; Nancy J. Vnuk, South Milwaukee; Murthy S. Munagavalasa, Racine; Stacey L. Forkner, Waterford; Daniel L. Hurrle, Menomonee Falls, all of Wis.

[73] Assignee: S. C. Johnson & Son, Inc., Racine, Wis.

[21] Appl. No.: 09/251,170

[22] Filed: Feb. 17, 1999

[51] Int. Cl.[7] .......................... A61M 16/00; A24F 25/00; A62B 7/08

[52] U.S. Cl. .............................. 392/390; 239/55; 422/125

[58] Field of Search ...................................... 392/386, 390, 392/391, 392, 393, 394, 395; 239/34, 35, 36, 37, 53, 54, 55, 56, 57; 422/125, 126

[56] References Cited

U.S. PATENT DOCUMENTS

| | | |
|---|---|---|
| 2,742,342 | 4/1956 | Dew et al. ................................. 422/37 |
| 3,558,055 | 1/1971 | Storchheim . |
| 4,145,001 | 3/1979 | Weyenberg et al. . |
| 4,157,787 | 6/1979 | Schwartz ..................................... 239/56 |
| 4,277,024 | 7/1981 | Spector ....................................... 239/36 |
| 4,439,415 | 3/1984 | Hennart et al. . |
| 4,544,592 | 10/1985 | Spector ....................................... 428/68 |
| 4,849,606 | 7/1989 | Martens et al. ........................... 392/390 |
| 5,556,192 | 9/1996 | Wang ......................................... 392/390 |
| 5,645,845 | 7/1997 | Neumann et al. . |

*Primary Examiner*—Sang Paik

[57] ABSTRACT

Disclosed herein are devices for dispensing volatile vapors such as insecticides. Table-like carrier members provide a compartment for the volatile material. One or more table leg structures extend down from a table top to support a cavity in the table top a distance above a burner element. This results in more moderate and uniform heating, thereby permitting efficient release of the volatile material over a longer period of time.

9 Claims, 2 Drawing Sheets

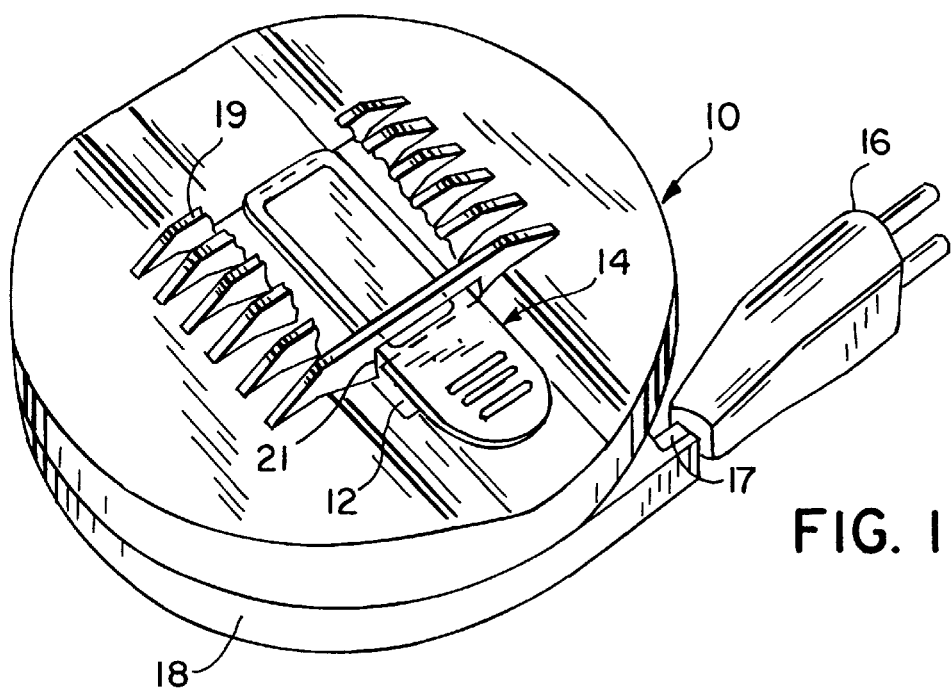
FIG. 1
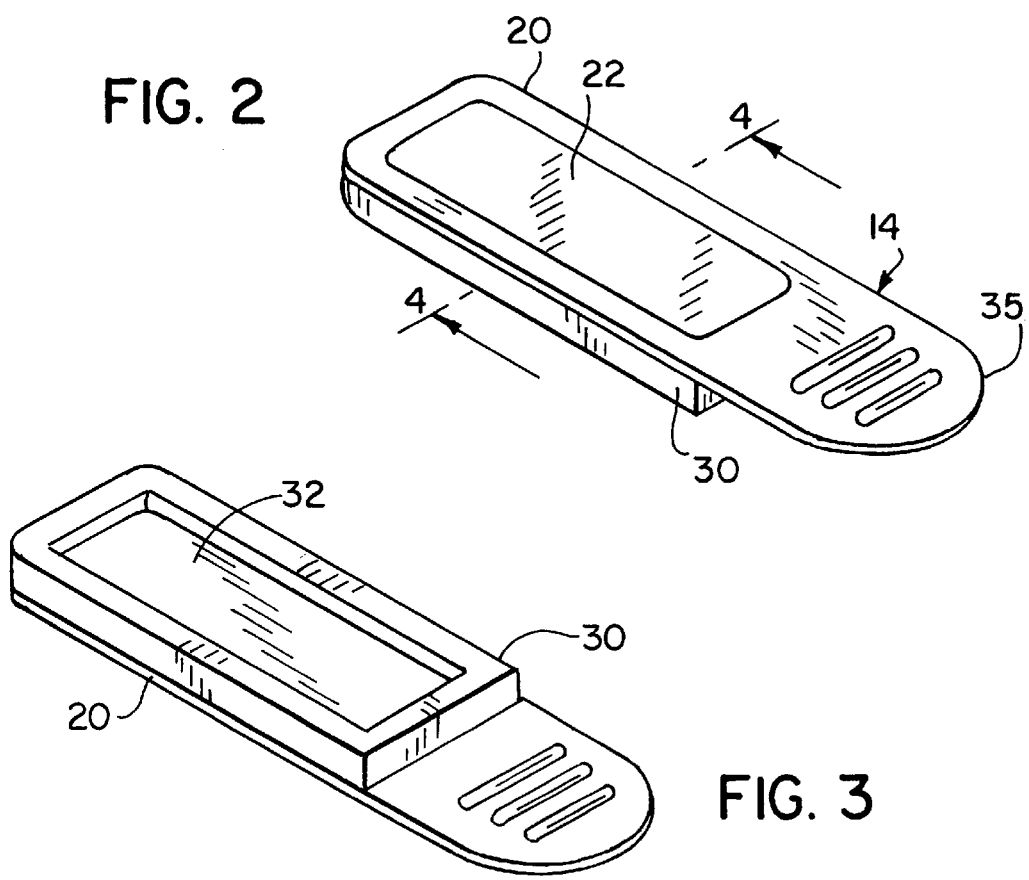
FIG. 2
FIG. 3

DEVICE FOR DISPENSING VOLATILE MATERIALS

CROSS REFERENCES TO RELATED APPLICATIONS

Not applicable.

STATEMENT REGARDING FEDERALLY SPONSORED RESEARCH

Not applicable.

BACKGROUND OF THE INVENTION

This invention relates to dispensing volatile materials such as insecticides, insect repellents, and fragrances. More particularly, it relates to devices containing a volatile material which are employed in conjunction with an electrical heating apparatus.

It is known in the art to impregnate a solid porous mat with a volatile material, or to place a volatile material in a pan-like metal structure. These mats and pans were placed on heaters to cause the volatile material to vaporize into the atmosphere. One type of heater used for this purpose was sold by S. C. Johnson & Son, Inc. under the trademark FUYI VAPE. See also U.S. Pat. No. 4,439,415 for a general discussion of heater units used for this purpose. The disclosure of this patent, and of all other publications referred to herein, are incorporated by reference as if fully set forth.

A problem with such metal pans is that for typical heaters they could cause the volatile material to be exposed to too much heat. This could cause the volatile to be used up too fast or to degenerate (particularly during extended usage).

The mats had similar problems, and also had significant problems with respect to the mats being exposed to different temperatures across the mat surface. In this regard, low-cost existing heaters often have hotter regions at certain points along their burner surface. The mats therefore had somewhat inefficient vaporization.

The above problems are of increased concern for products designed for use for a week or more. Merely adding additional volatile does not adequately address the problem as prolonged exposure of volatiles to too high temperatures wastes and/or destroys the volatile.

Another design consideration is that existing heaters, for safety and other reasons, often only accept inserts having a small cross-sectional shape (which fit into a small heater opening). Thus, any solution to the above problem needs to take into account size restrictions.

As such, it can be seen that a need exists for an improved volatile dispensing device.

BRIEF SUMMARY OF THE INVENTION

In one aspect, the invention provides a table which is suitable to dispense volatile vapors when heated. The table has a table top with a cavity in its upper surface. A volatile material is placed in the cavity. A support extends downwardly from the table top, the support being constructed and arranged so as to be suitable to be placed on a surface of a heater while leaving an air gap between a bottom of the cavity and a heating surface of the heater. The support extends at least partially radially outward of the cavity (below and/or adjacent the sides of the cavity).

In one preferred form the volatile material is selected from the group consisting of insecticides, insect repellents, fragrances, and deodorizers, a solid substrate (such as cellulose) is positioned in the cavity, and the substrate is impregnated with the volatile material. Also, a porous membrane extends over the cavity, the table top is made of metal, and the support is made of plastic.

In another aspect, the invention provides a device for dispensing volatile vapors. There is a heater having a heating surface. A table of the above kind is positioned adjacent the heating surface. Preferably, the heater is an electrical resistance heater.

The present invention provides a way of holding the volatile up off the burner unit so that there is a temperature step-down before the bottom of the cavity is exposed to heat. Further, the air gap and metal structure serve to spread the heat more uniformly across the cavity. This leads to more efficient use of expensive volatiles as well as reduces denigration due to excessive temperature. As a result, inserts can be designed for use for a week or even a month.

These and still other features and advantages of the present invention (e.g. combining such tables with such heaters) will be apparent from the description which follows. The following description is of the preferred embodiments. The claims should be looked to in order to understand the full scope of the invention.

BRIEF DESCRIPTION OF THE DRAWINGS

FIG. 1 is a top, partially-fragmented, perspective view showing a device for dispensing volatile materials of the present invention;

FIG. 2 is a top perspective view of the table of FIG. 1;

FIG. 3 is a bottom perspective view of the table of FIG. 1;

DETAILED DESCRIPTION

Figure 4:
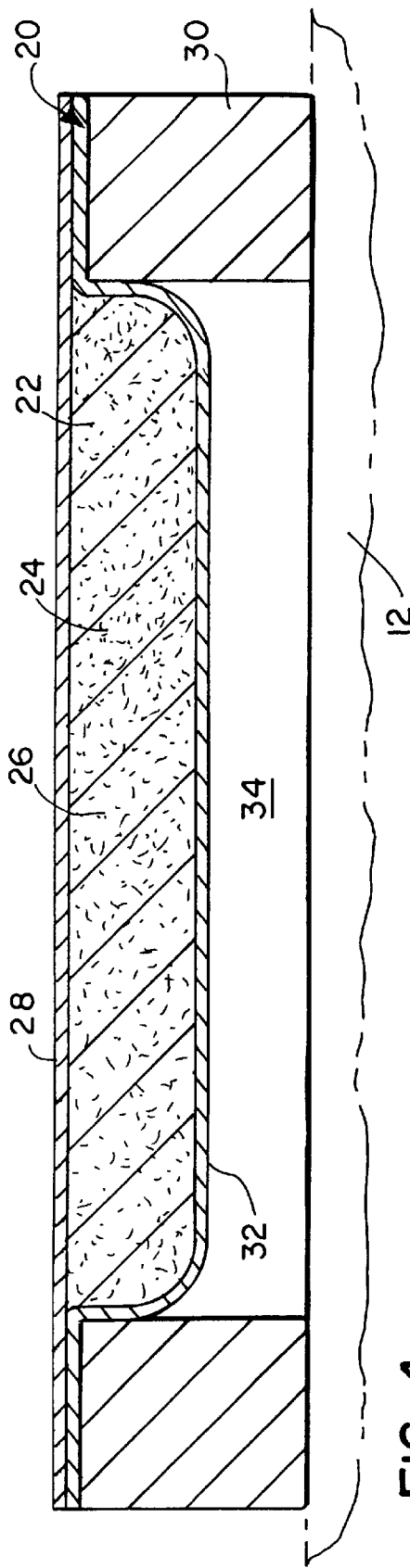
FIG. 4 is a sectional view taken along line 4—4 of FIG. 2.

In FIG. 1 there is shown an electrical heater, generally 10. The heater is the FUYI VAPE heater previously described, except that the mat previously used with that heater has been replaced with a table of the present invention. The heater is an electrical-resistance heater, and has a flat, upwardly exposed plate 12 adjacent to which is placed a table 14 of the present invention.

An electrical plug 16 (preferably of the self-retracting type) supplies electricity to the heating plate 12 by means of electrical cord 17. During non-use it is almost entirely contained in lower housing 18. As shown at 21, six safety grids are provided (five of which are broken away in FIG. 1 for purposes of illustration).

Referring now to FIGS. 2–4, table 14 has a table top 20 made of aluminum (or other metal) having an upwardly-facing cavity 22. A solid substrate 24 is made of a porous material such as paper or other cellulose-based material. Other solid porous substrates could also be used, such as sintered glass, plastic beads, natural or synthetic fabrics, and other absorbent and adsorbent materials. The substrate/mat 24 is impregnated with a volatile 26 and then placed in the cavity 22. The volatile is released from the substrate 24 when the table is heated.

Extending over the open portion of cavity 22 and substrate 24 is a porous or semi-porous membrane 28 which is preferably a laminated membrane having an lower layer which is polyethylene terephthalate and an upper layer which is polyethylene. Membrane 28 further slows release of the volatile 26 from the substrate 24 when the substrate is heated by the heating plate 12.

For long-term storage (e.g. on a retailer's shelf), a non-porous removable cover (not shown) is placed over layer 28. See e.g. U.S. Pat. No. 4,145,001.

Extending downwardly from table top 20 is a support 30, which in one embodiment surrounds the sides of the lower portion of cavity 22. It should, at minimum, have a portion that extends farther outward than the bottom of the cavity 22. In this regard, by "radially outward" we mean that some portion of the structure is radially outward, regardless of whether at the side or below the cavity. In an especially preferred form, none of the support is immediately below the cavity.

The support can be made of an insulative material such as a temperature-resistant cellulosic material or foam or other heat resistant and flame retardant plastic. It can be secured to the table top by a friction fit around the sides of the cavity, by an adhesive such as epoxy, urethane, or acrylic adhesive, or by other means such as double sided tape.

The support 30 is designed to rest on heating plate 12, preferably straddling the burner surface. It thereby supports the cavity 22 and the bottom wall 32 (and thus the volatile) above the heating plate 12 with an air gap 34 therebetween. There can also be a tab/handle 35 extending from table top 20 for facilitating the insertion and removal of the table 14 on burner plate 12 under safety grids 19 (as illustrated in FIG. 1).

Figure 5:
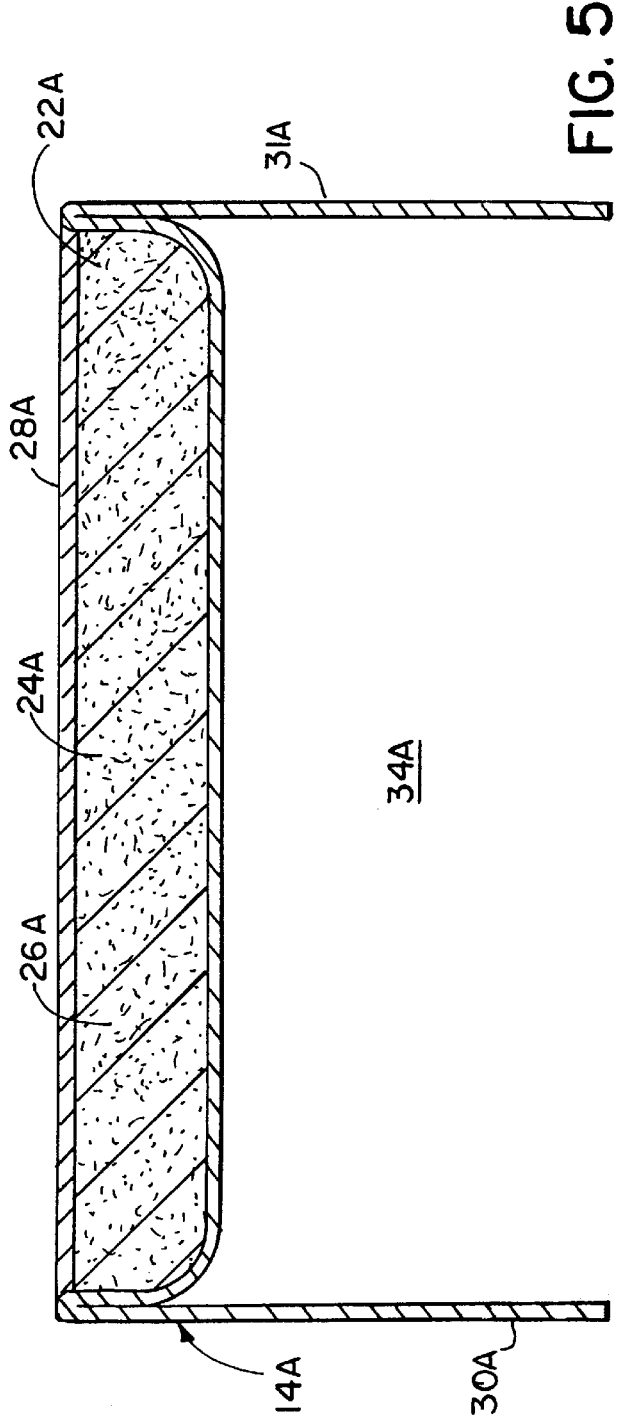
FIG. 5 is a sectional view of an alternative embodiment of a table of the present invention.

An alternative embodiment 14A is shown in FIG. 5 where similar numerals designate similar components, except with the numerals having an "A" suffix. The difference between embodiments 14 and 14A is in the use of a different support. Support 30A is composed of the same material as top 20A (preferably both aluminum). It is formed as one piece during a stamping operation, albeit it has two opposing table legs 30A and 31A which can be bent to positions shown in FIG. 5 (to provide support of the cavity 22A above a heating plate).

An important feature of the invention is that at least part of the support (preferably all) is not directly under the cavity, so as to thereby create an air gap. This gap slows heat transfer from the heating plate 12, and thus creates a step-down in temperature from the burner plate temperature (with a resulting slower release of insecticide and less heat-caused degradation of insecticide). This slower release, assisted by porous membranes 28 and 28A, results in sustained release of the insecticide over a longer period, thereby permitting inserts to be created which can be effectively used for a week or longer.

While insecticide 26 has been illustrated in conjunction with the impregnation of a solid substrate 24, a liquid or gel could be used without the solid substrate, in conjunction with porous membrane 28. See e.g. U.S. Pat. No. 5,645,845 for gel-based systems. In one form, we used a mixture of transfluthrin with a silica gel such as the gel sold under the trade name Cabosil.

The volatile material is preferably one of (or mixtures of) known insecticides and insect repellents. Particularly preferred are organic phosphorous insecticides, lipidamide insecticides, natural repellents as citronella oil, natural pyrethrins and pyrethrum extract, and synthetic pyrethroids. Suitable synthetic pyrethroids are acrinathrin, allethrin as D-allethrin, Pynamin®, benfluthrin, bifenthrin, bioallethrin as Pynamin Forte®, S-bioallethrin, esbiothrin, esbiol, bioresmethrin, cycloprothrin, cyfluthrin, beta-cyfluthrin, cyhalothrin, lambda-cyhalothrin, cypermethrin, alpha-cypermethrin, beta-cypermethrin, cyphenothrin, deltamethrin, empenthrin, esfenvalerate, fenpropathrin, fenvalerate, flucythrinate, taufluvalinate, kadethrin, permethrin, phenothrin, prallethrin as Etoc®, resmethrin, tefluthrin, tetramethrin or tralomethrin. Other volatile insecticides as described in U.S. Pat. No. 4,439,415 can also be employed. Most preferred is transfluthrin.

Deodorizers may also be used such as a terpene based deodorizer fragrance.

Further, disinfectants may be used such as glycols, trimethylene, and dipropylene. In addition, organic acids which are compatible with the use of the substrate and the atmosphere can also be utilized.

It should be understood that terms such as top and downwardly/bottom are used herein with respect to the most typical orientation. However, for heater units with vertical or other heating surfaces these terms are intended to mean directions away from and toward the heater, respectively.

While support section 30 has been shown as a continuous, uninterrupted ring, if desired it also could be a series of leg-like projections (with spacing in between). Thus the invention is not to be limited to the specific embodiments shown. Rather, the claims should be looked to in order to appreciate the full scope of the claimed invention.

INDUSTRIAL APPLICABILITY

The invention provides a device for dispensing volatile materials such as insecticides. The device is particularly useful in controlling mosquitoes over extended periods.

We claim:

1. A table that is suitable to dispense volatile vapors when heated, the table comprising:

a table top having in its upper surface a cavity having a bottom wall;

a volatile material placed in the cavity and supported on the bottom wall; and a support extending downwardly from the table top, the support being constructed and arranged so as to be suitable to be placed on a surface of a heater while leaving an air gap extendable between a bottom of the cavity and a heating surface of the heater;

wherein the support extends at least partially radially outward of the cavity.

2. The table of claim 1, wherein the volatile material is selected from the group consisting of insecticides, insect repellents, fragrances, and deodorizers.

3. The table of claim 1, wherein a porous solid substrate is positioned in the cavity and the volatile material impregnates the substrate.

4. The table of claim 3, wherein a gel mixed with the volatile is positioned in the cavity.

5. The table of claim 4, further comprising a porous membrane extending over the cavity.

6. The table of claim 1, wherein the table top is made of metal.

7. The table of claim 1, wherein the support is made of plastic.

8. A device for dispensing volatile vapors, comprising:

a heater having a heating surface; and a table of claim 1 positioned adjacent the heating surface.

9. The device of claim 8, wherein the heater is an electrical resistance heater.

* * * * *